(12) United States Patent
Andersen

(10) Patent No.: US 8,707,040 B2
(45) Date of Patent: Apr. 22, 2014

(54) ESTABLISHING SECURE COMMUNICATION BETWEEN AN IMPLANTABLE MEDICAL DEVICE AND AN EXTERNAL DEVICE

(75) Inventor: Dean P. Andersen, San Jose, CA (US)

(73) Assignee: NeuroPace, Inc., Mountain View, CA (US)

( * ) Notice: Subject to any disclaimer, the term of this patent is extended or adjusted under 35 U.S.C. 154(b) by 204 days.

(21) Appl. No.: 13/286,065

(22) Filed: Oct. 31, 2011

(65) Prior Publication Data
US 2013/0108046 A1 May 2, 2013

(51) Int. Cl.
*H04L 29/06* (2006.01)

(52) U.S. Cl.
USPC .......................................................... 713/169

(58) Field of Classification Search
None
See application file for complete search history.

(56) References Cited

U.S. PATENT DOCUMENTS

| | | | |
|---|---|---|---|
| 7,155,290 B2 | 12/2006 | Von Arx et al. | |
| 7,475,245 B1 | 1/2009 | Healy et al. | |
| 7,818,067 B2 | 10/2010 | Healy et al. | |
| 7,890,180 B2 | 2/2011 | Quiles | |
| 2003/0021411 A1* | 1/2003 | Seroussi et al. | 380/46 |
| 2005/0228693 A1 | 10/2005 | Webb et al. | |
| 2007/0282398 A1* | 12/2007 | Healy et al. | 607/60 |
| 2008/0044014 A1* | 2/2008 | Corndorf | 380/37 |
| 2008/0288029 A1 | 11/2008 | Healy et al. | |
| 2009/0326610 A1 | 12/2009 | Pless et al. | |
| 2010/0085160 A1* | 4/2010 | Fu | 340/10.1 |
| 2011/0171905 A1* | 7/2011 | Roberts et al. | 455/41.1 |

OTHER PUBLICATIONS

U.S. Appl. No. 12/554,959, filed Sep. 7, 2007.
"Data Encryption Standard (DES)", Federal Information Processing Standards Publication 46-2, (Dec. 30, 1993).
Volkmer, Markus et al., "Lightweight Key Exchange and Stream Cipher based solely on Tree Parity Machines", European Network of Excellence for Cryptology Workshop on RFID and Lightweight Crypto, Graz University of Technology, Graz, Austria, (2005).
"Announcing the Advanced Encryption Standard (AES)", Federal Information Processing Standards Publication 197,(Nov. 26, 2001).
Halperin, Daniel et al., "Pacemakers and Implantable Cardiac Defibrillators: Software Radio Attacks and Zero-Power Defenses", IEEE Symposium on Security and Privacy, (2008).
Paar, Christof et al., "Understanding Cryptography", A Textbook for Students and Practitioners. Springer-Verlag Berlin Heidelberg, (2010).

\* cited by examiner

*Primary Examiner* — David Pearson
(74) *Attorney, Agent, or Firm* — Arent Fox LLP

(57) ABSTRACT

Establishing secure communication between an implantable medical device and an external device includes: accessing, at the implantable medical device, biological data; utilizing the biological data, at the implantable medical device, to generate a public cryptographic key; and utilizing the public cryptographic key, at the implantable medical device, to generate a private cryptographic key.

32 Claims, 11 Drawing Sheets

ESTABLISHING SECURE COMMUNICATION BETWEEN AN IMPLANTABLE MEDICAL DEVICE AND AN EXTERNAL DEVICE

REFERENCE TO RELATED APPLICATIONS

The issued U.S. Pat. No. 6,810,285, entitled "Seizure Sensing and Detection Using an Implantable Device" by Pless et al., filed Jun. 28, 2001 and issued Oct. 26, 2004, co-owned by and assigned to the assignee of the present invention, is hereby incorporated by reference as background material. The U.S. patent application Ser. No. 12/554,959, entitled "Systems and Methods for Interacting with an Implantable Medical Device" by Pless, et al., filed Sep. 7, 2009, co-owned by and assigned to the assignee of the present invention, is hereby incorporated by reference as background material.

FIELD OF THE INVENTION

The present technology relates generally to data exchange session authentication, and more particularly, to a system and method for establishing secure communication between an implantable medical device and an external device.

BACKGROUND

Epilepsy, a neurological disorder characterized by the occurrence of seizures (specifically episodic impairment or loss of consciousness, abnormal motor phenomena, psychic or sensory disturbances, or the perturbation of the autonomic nervous system), is debilitating to a great number of people. It is believed that as many as two to four million Americans may suffer from various forms of epilepsy. Research has found that its prevalence may be even greater worldwide, particularly in less economically developed nations, suggesting that the worldwide figures for epilepsy sufferers may be in excess of one hundred million.

Since epilepsy is characterized by seizures, its sufferers are frequently limited in the kinds of activities in which they may participate. Epilepsy can prevent people from driving, working, or otherwise participating in much of what society has to offer. Some epilepsy sufferers have serious seizures so frequently that they are effectively incapacitated.

Current treatment of neurological disorders, particularly epilepsy, typically involves drug therapy and surgery. Additionally, electrical stimulation is an emerging therapy for treating epilepsy. Available electrical stimulation devices apply continuous electrical stimulation to neural tissue surrounding or near implanted electrodes. Moreover, electrical stimulation devices may be wirelessly accessed and programmed.

The drawings referred to in this description should not be understood as being drawn to scale unless specifically noted.

DESCRIPTION OF EMBODIMENTS

Various embodiments are described below, with reference to detailed illustrative embodiments, in the context of an implantable medical device disposed between the epidermis and the skull or within the cranium of a human patient. It will be apparent from the description provided herein that the systems, apparatuses and methods can be embodied in a wide variety of forms. Consequently, the specific structural and functional details disclosed herein are representative and do not limit the scope of embodiments of the present technology.

Overview of Discussion

Example systems and methods for establishing a secure communication between an implantable medical device (IMD) and an external device, such as a programmer, are described herein. The discussion begins with a description of an example IMD shown implanted within a patient. The discussion continues with a description of various components within an example IMD for establishing secure communications between the IMD and the programmer. An example method, utilizing the IMD, for establishing a secure communication between the IMD and the programmer is then described. Discussion then turns to a description of additional example system for establishing secure communication between devices. Finally, additional example methods of operation are discussed.

Example IMD Implanted in a Patient

Figure 1:
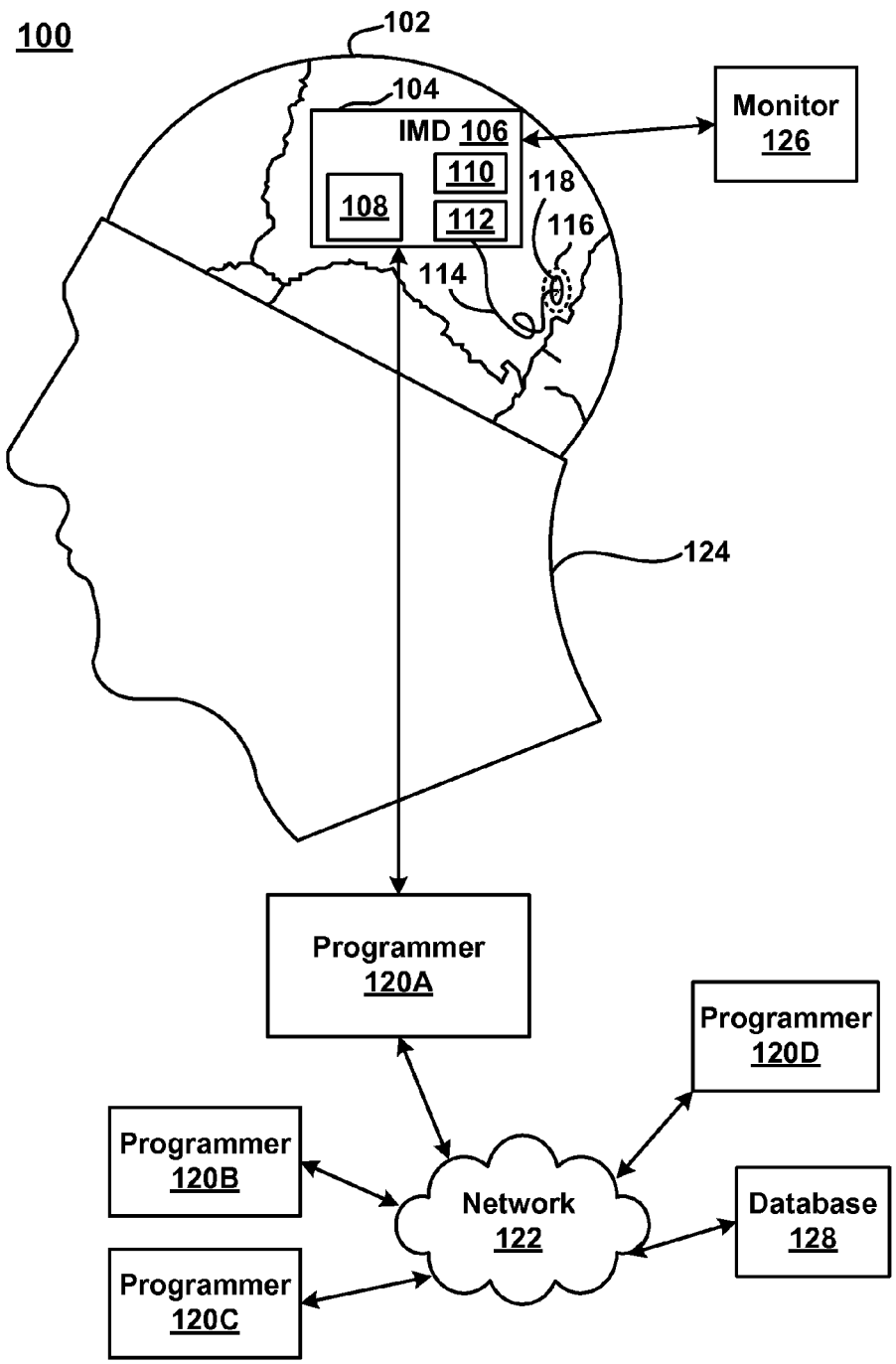
FIG. 1 is a block diagram illustrating an implantable medical device implanted in a patient and its use environment, in accordance with an embodiment.

FIG. 1 illustrates an IMD 106 implanted in a patient 124, in its use environment 100, according to an embodiment. In general, the IMD 106 is able to detect and/or predict neurological events, record and/or log neurological events, and provide data useful in the diagnosis of a neurological disorder. More particularly, for example, the IMD 106 is able to detect seizures and/or their onsets or precursors within a patient 124.

In embodiments, the IMD 106 records neurological signals, such as electroencephalographic (EEG) signals and electrocoritcographic (ECoG) waveforms, detects and analyzes EEG signals, and/or creates a log of such an analysis. In general, EEG signals represent aggregate neuronal activity potentials detectable via sensors applied to a patient's scalp. ECoG signals, which are deep-brain counterparts to the EEG signals, are detectable via sensors implanted on or under the dura mater, and usually within the patient's brain. Unless otherwise noted herein, the term "EEG" shall be used generically herein to refer to both EEG and ECoG signals.

The IMD is programmable and typically has a relatively large number and variety of parameters that can be set and subsequently be modified in a programming session after the IMD 106 is implanted in a patient. Thus, for example, the IMD 106 may be programmed to begin recording detected EEG signals satisfying certain detection parameters or criteria (e.g., based on a combination of parameter values) from the patient 124 at the onset or as a result of a prediction of ictal activity. The IMD 106 may be configured to record signals or values corresponding or related to signals at times before, during and after the detection criteria have been met. The IMD 106 may continue recording until the ictal activity stops. Optionally, the IMD 106 saves the recording, or a sampling of it, to a memory device to preserve it for later downloading to the external device. The IMD 106 may also create a log of the ictal activity. In one example, the IMD 106 records and/or logs the date and time when an event begins and ends, the duration of the event, indications of the intensity of the event, etc. The IMD 106, optionally, downloads such a log to an external device, such as, but not limited to, a programmer 120 (described in greater detail below). The IMD 106 may also be configured to record and/or preserve data corresponding to EEG signals upon the initiation of some action (e.g., swiping an external magnet near the site at which the IMD 106 is implanted) by the patient, a caregiver or physician.

In some embodiments, the IMD 106 detects and/or predicts any kind of neurological event that has a representative electrographic signature. While an embodiment is described herein as responsive to epileptic seizures, it should be recognized that the IMD 106 can respond to other types of neurological disorders, such as movement disorders (e.g., the tremors characterizing Parkinson's disease), migraine headaches, chronic pain and neuropsychiatric disorders (e.g., depression). In various embodiments, an IMD 106 detects neurological events representing any or all of these afflictions when they are actually occurring, in an onset stage, and/or as a predictive precursor before clinical symptoms begin.

Referring still to FIG. 1, the IMD 106 is shown as implanted between a patient's epidermis and skull. However, it should be appreciated that the placement described and illustrated herein is merely an example. Other locations and configurations are also possible, depending on the size and shape of the device and the patient's needs, among other factors.

Generally, the IMD 106 is positioned to follow the contours of a patient's cranium 102. However, other locations within the patient's body are also possible. For example, the IMD 106 can be implanted pectorally (not shown) with leads extending through the patient's neck and between the patient's cranium 102 and epidermis.

With continued reference to FIG. 1, the IMD 106 includes a housing 104 that encapsulates a control module 108. The control module 108 detects and/or records the desired neurological signals. Additionally, the IMD 106 may include at least one sensor 118 (e.g., an electrode or other transducer) that is sensitive to a physiological signal (e.g., electrical neurological signals and/or signals corresponding to body movement). The at least one sensor 118 may be formed from, for example, but not limited thereto, a platinum member. While in one embodiment, the at least one sensor 118 may be incorporated into the housing 104, in another embodiment, the at least one sensor 118 may be connected to the electronics within the housing 104 by a lead wire 114 implanted in or on the brain or upon the dura at a seizure onset location 116 so that the IMD 106 does not need to be located at the focus of the seizure onset location 116. A separate lead can also be used if the seizure onset location is in an area of the brain where the housing 104 cannot be implanted due to surgical constraints. A separate lead may also be an option in the event that there are two seizure foci in disparate locations and only one seizure focus would be apparent to the sensor incorporated into the housing 104.

The housing 104 may be fabricated from a biocompatible material, such as, but not limited to, titanium. Titanium is light, extremely strong and biocompatible. Other biocompatible materials may additionally or alternatively be utilized in the fabrication of the housing 104.

The housing 104 may also enclose a battery 110, as well as the control module 108 (described below in greater detail). Further, a telemetry antenna (not shown) may be provided inside or outside of the housing 104 (and potentially integrated with a lead wire 114 connecting the at least one sensor 118 to the housing 104) to facilitate communication between the IMD 106 and one or more external devices. Of note, the one or more external devices may be, but are not limited to the following: one or more programmers; and one or more monitors (e.g., a patient remote monitor). (See FIG. 1, programmers 120A, 120B, 120C and 120D [hereinafter referred to as "programmer 120", unless specifically noted otherwise], and monitor 126). The programmer 120 may be any apparatus that is capable of communicating instructions and/or sharing data information with the IMD 106, such as, but not limited to, a laptop, a desktop, and a hand-held computer.

As noted above and as illustrated in FIG. 1, the IMD 106 may operate in conjunction with an external device. The IMD 106 performs, for the most part, autonomously (particularly when performing its usual sensing, detection, and recording capabilities), but includes the capability to establish a wireless link to an external device (e.g., programmer 120).

In one embodiment, the wireless link may be established by moving a wand (or other apparatus) into the transmitting and receiving range of the IMD 106. The wand has communication capabilities and is coupled with the programmer 120. The programmer 120 may then be used to control the operation of the IMD 106, as well as to transmit information to and/or receive information from the IMD 106.

Several specific capabilities and operations performed by the programmer 120 in conjunction with the IMD 106 may include, but are not limited to, the following: specifying and setting variable parameters in the IMD 106 to adapt the function of the IMD 106 to meet the patient's needs; downloading and/or receiving data (including but not limited to stored EEG waveforms, parameters, or logs of events detected) from the IMD 106 to the programmer 120; uploading and/or transmitting program code and other information from the programmer 120 to the IMD 106; and commanding the IMD 106 to perform specific actions and/or change modes, as instructed by a physician operating the programmer 120. To facilitate these functions, the programmer 120 is adapted to receive physician input and provide physician output. Further, data is transmitted between the programmer 120 and the IMD 106 over the wireless link.

In one embodiment, the programmer 120 is coupled with a network 122, such as the Internet, via a communication link. This allows information that is downloaded from the IMD 106, as well as program code (or other information) to be uploaded to the IMD 106, to be stored in a database 128 at one or more data repository locations (which may include various servers and network-connected programmers). This allows the patient 124 (and the patient's physician) to have access to important data, including past treatment information and software updates, essentially anywhere in the world that there is a programmer (e.g., programmer 120) and a network connection.

The IMD 106 may also have a sensor (not shown) configured to detect a magnetic field. For example, such a sensor can be configured to be triggered by a magnet moved into the vicinity of the IMD 106 by the patient 124 or caregiver when the patient 124 is experiencing clinical symptoms of a seizure or other significant neurological event. The IMD 106 may additionally then store an ECoG sample that would be indicative of the seizure or neurological event. These magnet-triggered ECoGs could then be analyzed to program the detection parameters.

Example IMD and Various Components Therein

Figure 2:
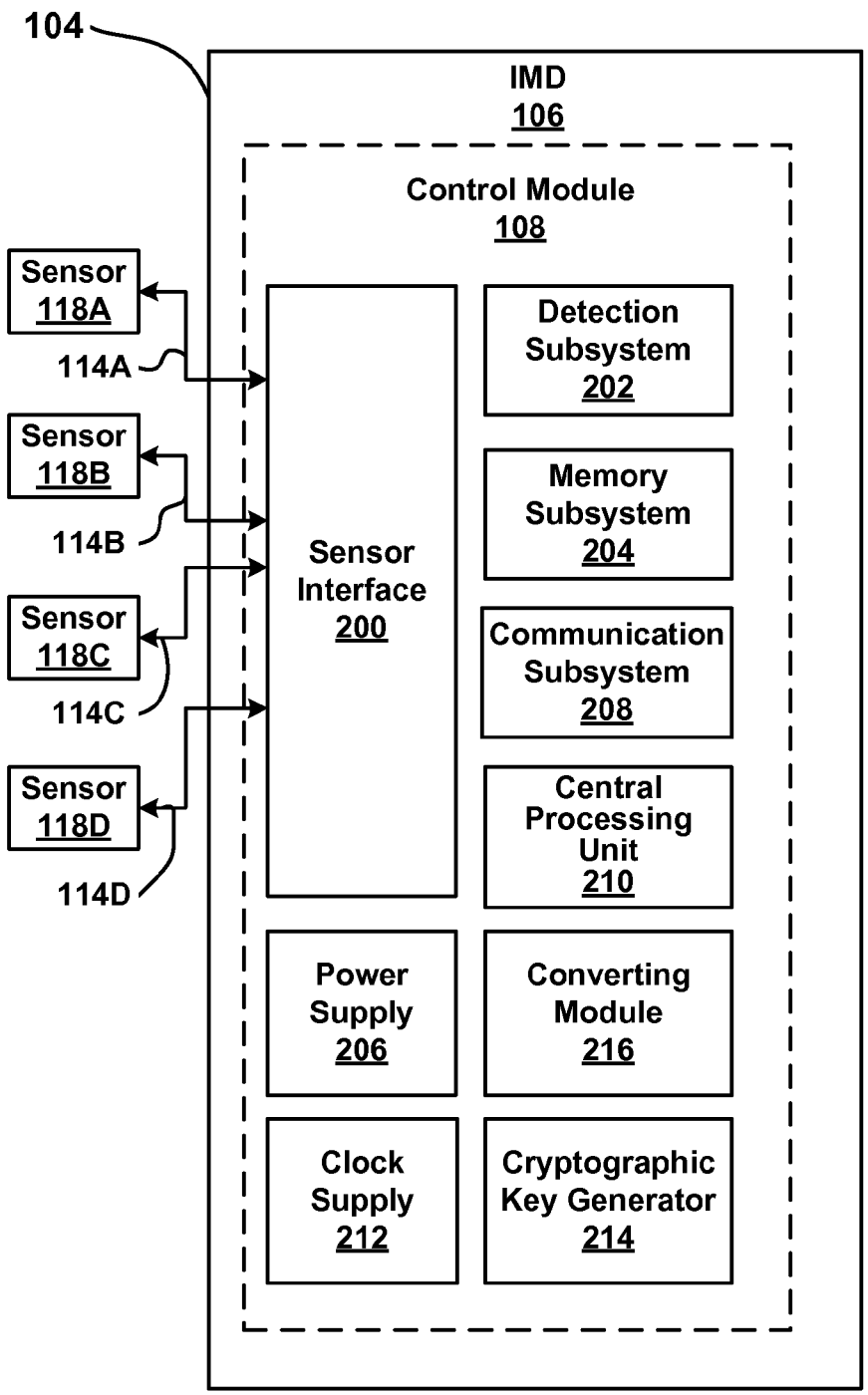
FIG. 2 is a block diagram illustrating components of an implantable medical device, in accordance with an embodiment.

FIG. 2 illustrates a block diagram of the example IMD 106 of FIG. 1, including components therein, used for measurement, detection, and/or recording, according to an embodiment. Several subsystems are disposed within the housing 104, thereby forming a control module 108. The control module 108 is coupled with a set of sensors (i.e., electrode[s]) 118A, 118B, 118C and 118D (hereinafter, "sensor(s) 118", unless noted otherwise) via leads 114A, 114B, 114C and 114D, respectively (hereinafter, "lead wire 114", unless noted otherwise). Although four sensors 118, each with its own lead, are depicted in FIG. 2, embodiments are well suited to utilizing a greater or lesser number of either the sensors 118, the leads 114 or both. Embodiments also are well suited to using multiple sensors 118 on a single lead 114.

As shown in FIG. 2 and in accordance with an embodiment, the control module 108, coupled with sensor(s) 118, includes a converting module 216, a cryptographic key generator 214, and optionally one or more of the following: a sensor interface 200; a detection subsystem 202; a memory subsystem 204; a communication subsystem 208; a central processing unit (CPU) 210; a power supply 206; and a clock supply 212.

The sensor(s) 118 are connected to the sensor interface 200. The sensor interface 200 is capable of selecting one or more of sensor(s) 118 as is required for sensing. Accordingly, the sensor interface 200 is coupled with the detection subsystem 202. The sensor interface 200 may also provide other features/capabilities, including but not limited to the following: amplification; isolation; and charge-balancing functions (that can be used for a proper interface with neurological tissue and may not be provided by any other subsystem within the IMD 106). In still other embodiments, where a sensor 118 is an electrode, the sensor interface 200 may be used to switch the function of an electrode from a sensing function to a stimulation function, where the IMD 106 is used for both sensing and electrical stimulation.

In one embodiment, the detection subsystem 202 includes an EEG analyzer function. In one such embodiment, the EEG analyzer function is adapted to receive EEG signals from the sensor(s) 118, through the sensor interface 200, and to process those EEG signals to identify neurological activity indicative of a seizure, an onset of a seizure, and/or a precursor to a seizure.

The detection subsystem 202, in one embodiment, also contains further sensing and detection capabilities, including but not limited to, parameters derived from other physiological conditions (such as electrophysiological parameters, temperature, blood pressure, movement, etc.).

The CPU 210 takes the form of a microcontroller, is coupled with the memory subsystem 204 and controls the operation of the memory subsystem 204, in one embodiment. In one such embodiment, the CPU 210 is also coupled with the detection subsystem 202 for direct control thereof. The memory subsystem 204 is coupled with the detection subsystem 202 and functions at least for receiving and storing data representative of sensed EEG signals and evoked responses.

The communication subsystem 208 is coupled with the memory subsystem 204 and the CPU 210, in one embodiment. The communication subsystem 208 enables communication between the IMD 106 and the outside world (see FIG. 1), and in particular, the programmer 120. As noted above, in some embodiments, the communication subsystem 208 includes a telemetry antenna (which may be situated inside or outside of the housing) enabling transmission and reception of signals, to and/or from an external apparatus, via inductive coupling. Alternative embodiments of the communication subsystem 208 may use an antenna for an RF link or an audio transducer for an audio link to the patient 124, in order to provide indications of neurological events, a system's status, and/or other relevant information.

The power supply 206 supplies the voltages and currents necessary for operation of each of the other subsystems. The clock supply 212 supplies substantially all of the other subsystems with any clock and/or timing signals needed for their operation.

It should be noted that while the memory subsystem 204 is illustrated in FIG. 2 as a separate functional subsystem, the other subsystems may also use various amounts of memory to perform the functions described herein, as well as other functions. Furthermore, while the control module 108 may be a single physical unit contained within a single physical enclosure, namely the housing 104, it may include a plurality of spatially separate units, each performing a subset of the capabilities described above. Also, it should be noted that the various functions and capabilities of the subsystems described herein may be performed by electronic hardware (e.g., hard wired modules), computer software (or firmware), or a combination thereof. The division of work between the CPU 210 and other functional subsystems may also vary—the functional distinctions illustrated in FIG. 2 may not reflect the integration of functions in a real-world system or method according to the embodiments disclosed herein.

The converting module 216 is coupled with the control module 108 and the set of sensor(s) 118, and converts a portion of sensed dynamic biometric activity to a digital representation (discussed below).

The cryptographic key generator 214 is coupled with the converting module 216 and generates a cryptographic key utilizing the digital representation (discussed below). In one embodiment, the cryptographic key generator 214 is also connected to the CPU 210.

As will be discussed below, as part of a cryptographically secure method of exchanging information between the IMD 106 and the programmer 120, embodiments of the present technology designate a portion of the digital representation of the sensed dynamic biometric activity as a random number (which becomes the public cryptographic key). In contrast, other approaches to generating a random number (and hence a public cryptographic key) require intensive computational steps that would drain the limited battery life of an IMD. Thus, embodiments provide a method and system for establishing secure communication between an IMD and a programmer (involving generating a public cryptographic key at the IMD) that optimizes use of the power source of the IMD.

Figure 3:
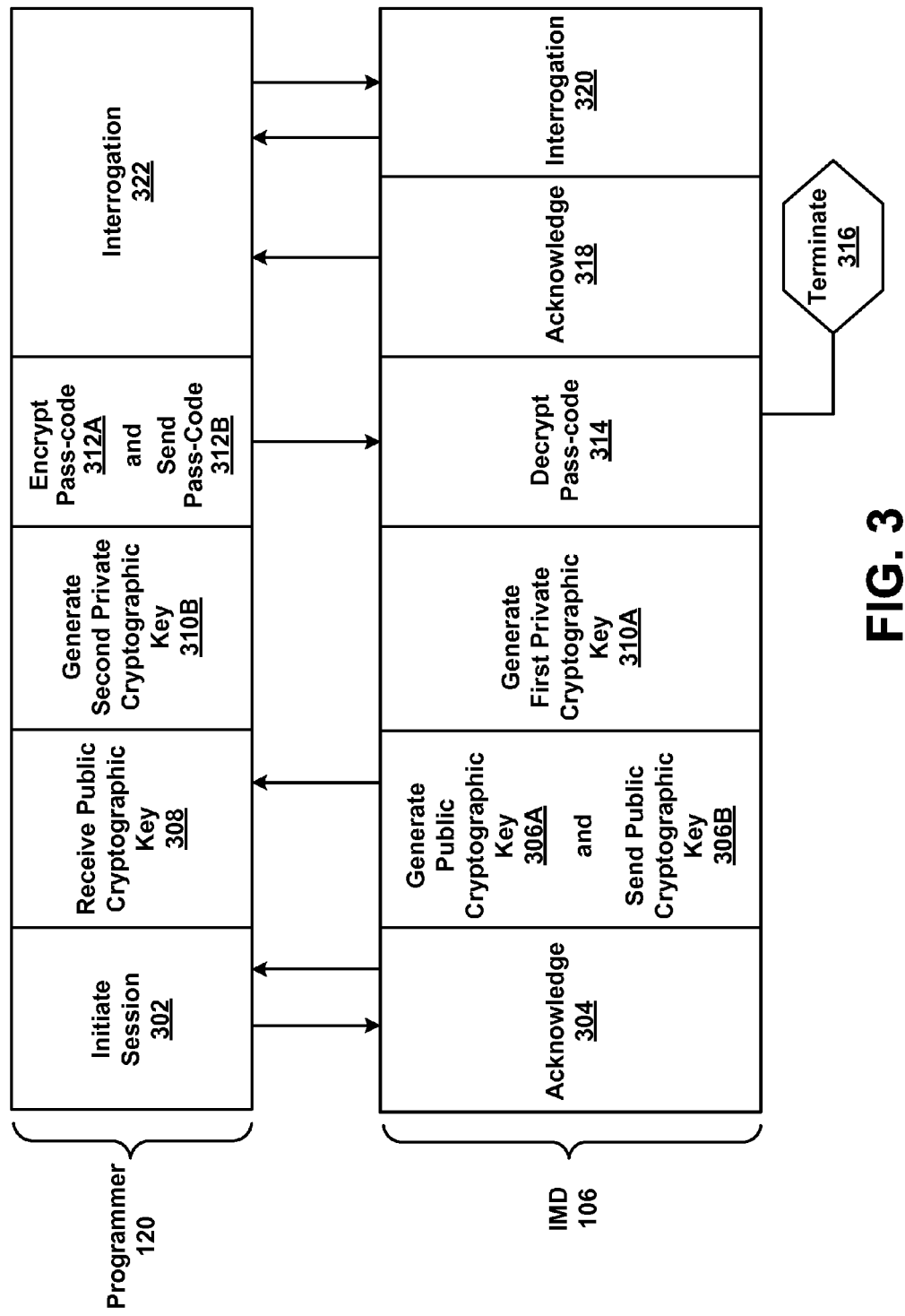
FIG. 3 is a flow diagram illustrating a method for establishing a secure communication between an implantable medical device and an external programmer, in accordance with an embodiment.

Example Method for Establishing Secure
Communication Between an IMD and a Programmer A discussion of an example method for establishing secure communication between an IMD and a programmer will begin with a description of current approaches for establishing secure communication and the limitations involved. The discussion will continue with a description of FIG. 3, illustrating a method 300 for establishing secure communication between the IMD and the programmer, in accordance with an embodiment.

Long-range (wireless) telemetry is an emerging form of communication between IMDs and external programmers and monitors. This communication can take place over several meters or even between rooms, with or without patient knowledge and/or participation. Thus, concerns have been raised about security and protection against the inadvertent interrogation and programming of an IMD that may leave the IMD is a state in which therapy is inhibited, or even maliciously programmed to harm a patient. Below are several examples of inadvertent and malicious interrogations of an IMD implanted in a patient.

In an example of an inadvertent programming of an IMD, consider several patients, X, Y and Z who are seated in a waiting room while a physician is in an examination room with patient A. The physician is attempting to program patient A's IMD. The physician is intending to use the same programmer (e.g., laptop computer) to manage and eventually program all of the patients, A, X, Y and Z. However, without an established secure communication channel between the physician's programmer and the IMD implanted in patient A's head, the physician may actually inadvertently program the IMDs implanted in patients X, Y, and Z.

In an example of an unwelcome but deliberate interrogation of a person's implanted IMD, consider a company attempting to access and collect the data saved in an IMD's memory. Without a way to establish a secure communication channel between the IMD and an external device, IMDs are susceptible to unwelcome data mining. In an example of a malicious programming of an IMD, consider an effort to reprogram implanted IMDs in such a way that the operations of the reprogrammed IMDs cause harm to their hosts. Again, without a way to establish a secure communication channel between an IMD and an external device, IMDs are susceptible to malicious interrogation.

Current approaches to securing information involve using standard encryption techniques, such as Advanced Encryption Standard (AES), Data Encryption Standard (DES) and Secure Hash Algorithm (SHA), to encrypt all messages between the programmer and the IMD. However, most encryption techniques are computationally intensive and costly, especially for the IMD, which is limited in terms of memory and CPU performance due to its power constraints. In other words, the performing of most encryption techniques at an IMD reduces the IMD's limited battery life. Also, the generating and storing of cryptographic keys becomes an issue; a cryptographic algorithm is only as strong as the secrecy of the cryptographic keys used for the algorithm.

One of the most difficult problems to solve in any encryption scheme is cryptographic key distribution. One of the fundamental principles in cryptography is Kerckhof's Principle, "All crypto algorithms must be public; only the keys are secret". For high security applications, such as in Internet security, the size of the public cryptographic key is very important since it determines the number of possible cryptographic keys. The larger the cryptographic key, the more difficult it is to crack. One approach to securing communicating information is to have a secret cryptographic key stored in both the IMD and the programmer. However, this approach is not good for security, since only one cryptographic key would be used at all times. Alternatively, another approach uses a series of, for example, n cryptographic keys stored in an IMD and a programmer. The cryptographic key exchange is a method of passing a parameter that identifies to both sides which is the valid cryptographic key of n number of cryptographic keys to use for the session. However, this approach presents difficulties in passing a cryptographic key index in a robust and secure fashion.

One of the most popular cryptographic key exchange protocols is the Diffie-Hellman key exchange. To use this approach, during each session, the IMD and the programmer software have to generate a random number, x. This random number is used to generate a cryptographic public key. The cryptographic key exchange algorithm takes a random number and two parameters (G and P) to make a public cryptographic key. Upon receiving the public cryptographic key, both the IMD and the programmer have to calculate the shared (also known as secret or private) cryptographic key. This approach can be computationally expensive since this requires finding the value of an exponential number. Depending on the size of the parameters (the larger the number the better for security), finding the value of the exponential number can be very time consuming. For example, if the public cryptographic key is 8-bits, and the random number is 8-bits, a worst case exponent would be $255^{255}$, approximately a 200 bit number. This can be done using multi-precision mathematics, which would be computationally complex if done in an IMD. To make this more manageable, smaller random numbers and prime numbers must be used. But using smaller random numbers and prime numbers would lead to diminished security since only a small finite set of numbers could be used.

Additionally, while other cryptographic key exchange approaches based on elliptical curve cryptography can lead to efficient implementation, these approaches are also very computationally complex.

As will be explained herein, through the use of random numbers culled from the byproduct of converting sensed dynamic biometric activity into a digital representation, embodiments provide a secure method of ensuring that only authorized devices can communicate with an IMD. More particularly, various embodiments utilize these random numbers to generate a public cryptographic key at the IMD. Thus, embodiments do not require the computationally intensive methods of generating random numbers needed for current encryption schemes. With reference now to FIG. 3, a flow diagram illustrating a method 300 for establishing secure communication between an IMD and a programmer is shown, in accordance with an embodiment, and will be described herein with reference to FIGS. 1 and 2.

At 302, the programmer 120 initiates a session with the IMD 106, in clear text. The term, "clear text", refers to an un-encrypted text or message. Of note, the IMD 106 includes the features as described with respect to the IMD described herein of FIGS. 1 and 2. At 304, the IMD 106 acknowledges the initiation of the session in clear text.

At 306A, the IMD 106 generates a public cryptographic key using a random number. The random number is generated from the converted digital representation of the sensed dynamic biometric activity. Further, a new random number is generated for every session between the IMD 106 and the programmer 120. In embodiments, the generation of the random number (that becomes the public cryptographic key) takes place without computation. That is, the random number is not a computer-generated random number. In one embodiment, for example, the generating of the public cryptographic key utilizing the random number refers to the designation of a predetermined portion of the random number (e.g., the last four digits, the last six digits, etc.) to be the public cryptographic key. A brief discussion of the random number generation immediately follows.

In general, creating a random number is a computationally intensive process and usually involves using special hardware. Most generic random number generators built into C language libraries, for example, are considered insecure and easily predictable. However, embodiments generate a random number without computation by utilizing biological signals and the concept of information entropy.

Information entropy refers to the inherent unpredictability of random numbers. Truly random numbers have high entropy. Biological signals can exhibit high levels of entropy. Thus, the random number associated with gathered biological signals is highly unpredictable. Classic EEG and EMG signals have high levels of entropy. In one embodiment, since an IMD is always recording ECoG data, a snippet(s) of this data may be used to generate the random number at the IMD. In another embodiment, a number based on metrics detected from the ECoG data is used, such as a number resulting from processing a line length between samples, for generating the random number at the IMD.

In yet another embodiment, data from other sensors, such as activity data from an activity sensor, can also be used to provide a random number. For example, data from an analog/digital converter (ADC) may give a digital representation of the ECoG data. In one such embodiment, the last four bytes of the ECoG data could be used to create a 4-byte random number to be used as the public cryptographic key. In a similar fashion, a greater or lesser number of bytes (or bits) of the ECoG data can be utilized to generate a longer or shorter random number. Alternatively, the ADC data is sent to a data processor (or similar component), where the line length between subsequent ECoG samples is determined. The last four bytes of the line length could be used to create a 4-byte random number. In a similar fashion, a greater or lesser number of bytes (or bits) of the line length can be utilized to generate a longer or shorter random number.

Thus, the sensing of dynamic biometric activity, such as ECoG data, automatically generates a random number, without requiring computation of the random number from scratch. As described herein, other methods of generating random numbers are computationally intensive, thus requiring a lot of power. Should the IMD itself perform a computationally intensive method of generating a random number, the task would cause a great strain on the IMD's limited power supply. As described herein, in one embodiment, the converting module 216 converts a portion of the sensed dynamic biometric activity into a digital representation that is used as the random number. Cryptographic key generator 214 uses this random number to generate a public cryptographic key.

At 306B, the IMD 106 sends this generated public cryptographic key to the programmer 120. At 308, the programmer 120 receives the public cryptographic key from the IMD 106. At 310A and 310B, the IMD 106 and programmer 120, respectively, generate a shared cryptographic key (a first private cryptographic key and a second private cryptographic key) using the public cryptographic key and a predetermined cryptographic key generation protocol. Another way to describe the private cryptographic key is as an encryption/decryption key; a parameter that both the encryption and decryption process uses as part of a cryptographic algorithm. In generating a private cryptographic key, the random number is transformed by a stream cipher.

A "stream cipher", for purposes of this application, refers to a stream of variable length data in which the encryption is performed. RC4 is an example of a predetermined cryptographic key generation protocol that uses stream ciphers. For stream ciphers, a linear feedback shift register (LFSR) is the basic building block. Stream ciphers do not have a fixed data length. The data length is determined by the algorithm chosen. Stream ciphers, based on scrambling a bit stream, have been used for wireless applications such as the A5/1 encryption used for GSM cellular networks. Stream ciphers are very low cost and typically implemented in hardware with simple LFSRs.

At 312A, the programmer 120 encrypts a pass-code with the second private cryptographic key. More particularly, the second private cryptographic key is used to transform a message (a string of data that includes the pass-code) into a string of encrypted text, also known as cipher text. If the IMD 106 and the programmer 120 did not use the shared cryptographic key, the encrypted data could not be decrypted without errors. Of note, a different cipher text is created with each session. At 312B, the programmer 120 sends the encrypted message, including the pass-code, to the IMD 106. Of note, the encrypted pass-code could not otherwise be sent in clear text (i.e., un-encrypted text or message) as it would be easy for an eavesdropper to decode this cryptographic key. Further, at 314, the IMD 106 decrypts the encrypted pass-code upon receipt from the programmer 120.

After the encrypted pass-code is decrypted by the IMD 106, the IMD 106 compares the decrypted pass-code to a "golden pass-code". The golden pass-code is programmed during the manufacturing of the IMD 106. Thus, in one embodiment, the golden pass-code is a fixed stream of data that the IMD 106 already knows and is stored in its non-volatile memory. The golden pass-code does not need to be unique for an external device, but possibly unique for a family. For example, a production model of both the IMD 106 and the programmer 120 may be considered to be of a "family". Of consequence, if the IMD 106 and the programmer 120 generate a first and second private cryptographic key, respectively, that are not the same, then the decrypted pass-code will not match the golden pass-code residing within the IMD's 106 internal memory.

Encrypting and decrypting every packet of data would be very CPU-intensive for the IMD. Thus, in some embodiments, only the encrypted pass-code that the programmer 120 sends gets decrypted and authenticated by the IMD 106. Once the pass-code is authenticated, the IMD 106 acknowledges the positive authentication status of the programmer 120. However, at 316, if it is shown through the authentication process that the pass-code is different than the golden pass-code known to the IMD 106, then the session between the IMD 106 and the programmer 120 is terminated. Note, while a different ciphertext is created with each session, the pass-code message remains the same.

At 318, the IMD 106 acknowledges that the authentication status of the programmer is positive and the programmer 120 is allowed access to and may share information with the IMD 106. At 320, the programmer 120 participates in the interrogation, sharing information, as has already been described herein. If communication between the programmer 120 and the IMD 106 gets lost due to a loss of signal, the session would have to begin again at 302, at the initiating stage.

Thus, various embodiments use "clear text" to open a channel, but a non-static pass-code to unlock the ability to read or write data to the IMD 106. The message (including the pass-code) is sent from the programmer 120 to the IMD 106 in cipher text, thereby making it difficult for an eavesdropper to decode the message. The message is encrypted with a different shared cryptographic key every time. Upon the IMD 106 decrypting and checking the pass-code, the IMD 106 either allows a programming session to begin or terminates the session.

One advantage over existing approaches for establishing secure communication is that a non-static data stream is used to unlock the interrogation and the programming of the IMD. Thus, each IMD and each session will have a dynamic data stream to be used to initiate an interrogation. Since each wireless session will exchange data based on a random number, the non-static data stream used to initiate an interrogation session is random with each IMD/programmer combination. Since embodiments do not store static keys and cryptographic keys are used only once, embodiments can more effectively withstand attacks, and thus create secure communication channels.

Yet another advantage that embodiments have over existing encryption techniques involves using a method and system having a low-computational overhead. Since the IMD only has to decrypt a single packet of data and not all the messages exchanged between the IMD and the external device, the IMD's computational burden is greatly eased. For example, once verification of a positive authentication status is indicated, the interrogation will send data in clear text without encryption/decryption. However, most other encryption/decryption schemes require numerous transformations of data packets. For example, AES requires ten such transformations. As a result, most hardware implementations of encryption schemes require several bus cycles to complete. This adds latency to communication data processing.

A further advantage of an embodiment is that the connection between a manufacturer's IMD and the manufacturer's external product may be authenticated. Additionally, embodiments enable a family of devices to share the same pass-code, instead of requiring a unique pass-code for each device.

Further, embodiments are able to circumvent attacks, such as but not limited to, brute-force attacks, cipher text attacks, and replay attacks.

A brute-force attack is one in which a programmer steps through up to every possible cryptographic key combination to gain access. For example, for a 64-bit key length, the number of attempts equals up to $2^{64}$ ($18 \times 10^{18}$) keys. The amount of power consumed by the RF circuitry (coupled with the IMD) during the brute-force attack by the programmer would most likely drain the IMD's primary cell battery before the private cryptographic key is discovered. Thus, by generating the private cryptographic key at the IMD instead of at an external device, a brute-force attack would most likely be unsuccessful (i.e., a private cryptographic key generated at the IMD is not discovered). More particularly, a typical A*hour primary cell has an energy of approximately 10,000 J. If the wireless RF circuit consumes a minimum of 100 µJ to wake up, then a total of only 100,000,000 attempts during a brute-force attack can be made before the IMD's battery becomes depleted. Thus, the IMD's battery life would most likely expire before a cryptographic key could be found, thereby circumventing the brute-force attack.

A cipher text attack tries to analyze the cipher text being passed and analyze the data, analyzing patterns and the frequency of reoccurrence of certain characters. However, the unique random number generation for every session circumvents the probing of the cipher text attack for patterns and character reoccurrence.

A replay attack tries the last known bit pattern used to open a channel. This type of attack would not be successful against embodiments described herein, since the IMD generates a unique random number for each session. In embodiments described herein, unless the random number for a current session is the same as a previous session, the occurrence of which holds a very low probability, the IMD is not subject to this type of attack.

Thus, various embodiments provide a novel method for establishing secure communications between an IMD and a programmer. Firstly, in an embodiment, a random number is developed from the sensed dynamic biometric activity as opposed to other methods (described herein) of generating a random number. Secondly, in an embodiment, the IMD, as opposed to an external device, is able to generate the random number. Thirdly, in an embodiment, the IMD's determination of the random number does not require the costly computational input that is required in other approaches of generating a random number. Fourthly, in an embodiment, the uniquely generated random number is used as the public cryptographic key and as part of the larger encryption/decryption process.

Example Systems

Figure 4A:
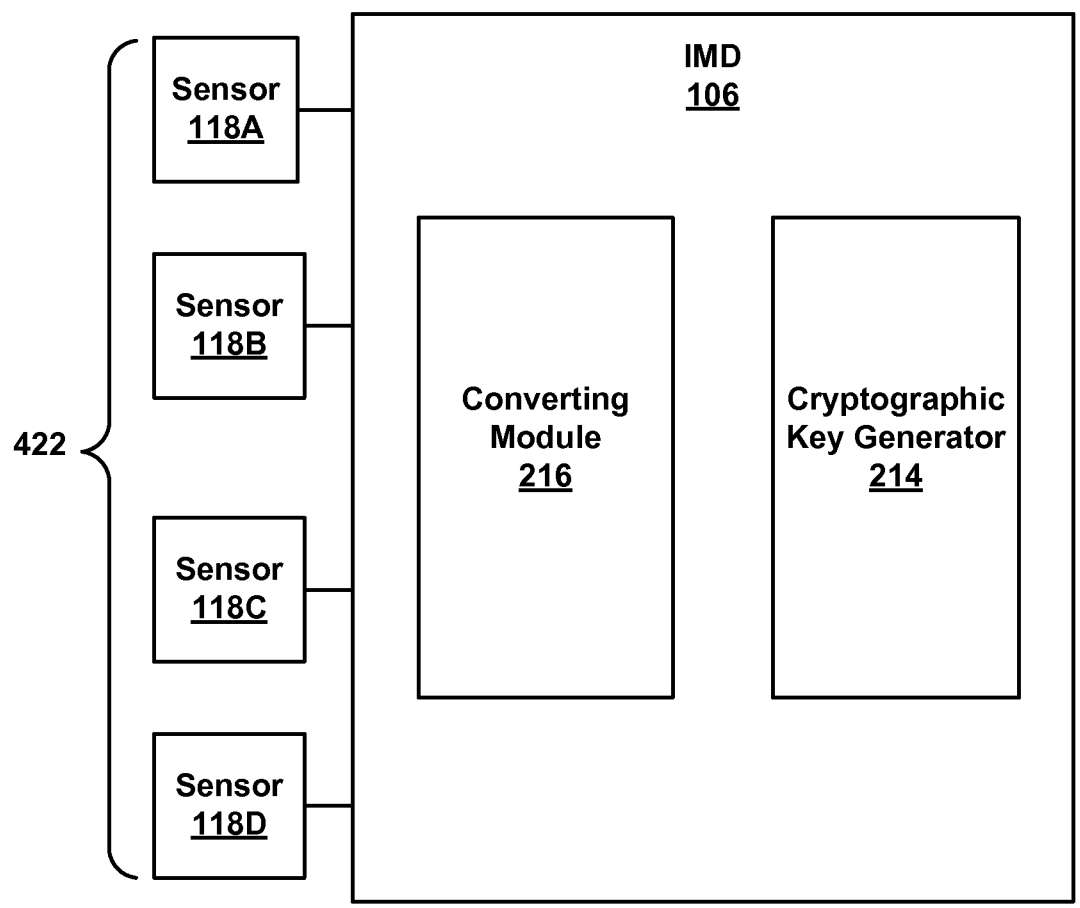
FIG. 4A is a block diagram illustrating a system, in accordance with an embodiment.

FIG. 4A is a block diagram illustrating a system 400, in accordance with an embodiment. The system 400 includes a set of sensor(s) (including sensors 118A, 118B, 118C and 118D in this example embodiment; hereinafter, "422"), a converting module 216 and a cryptographic key generator 214. Of note, the set of sensors 422 may be one or more sensors. The set of sensors 422 senses dynamic biometric activity. The term, dynamic biometric activity, refers to that activity relating to biological functions (e.g., EEG signals, physical body movements, physiological conditions, etc.) that can change with time. The converting module 216 is coupled with the set of sensors 422 and converts a portion of the sensed biometric activity into a digital representation.

Figure 4B:
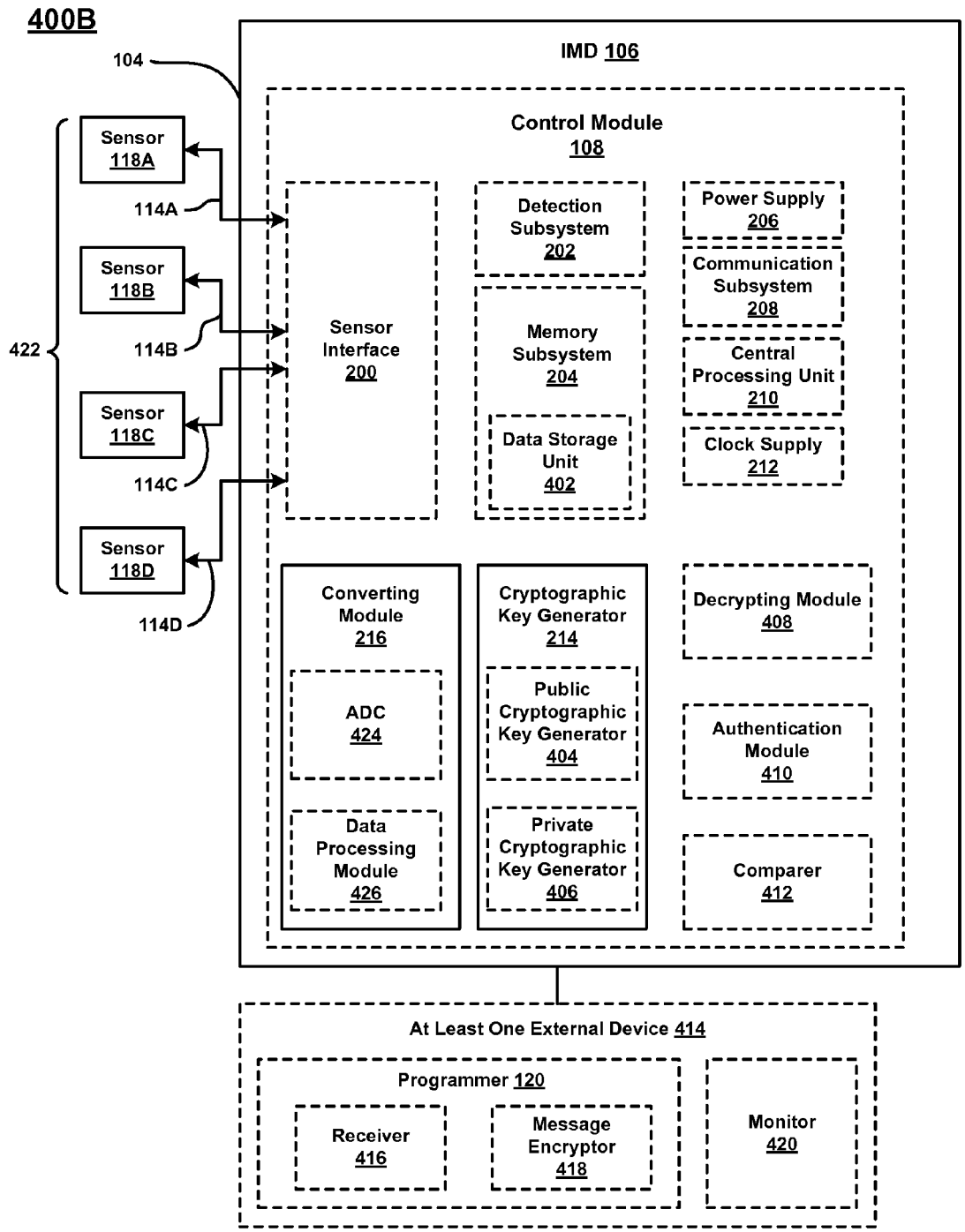
FIG. 4B is a block diagram illustrating a system, in accordance with an embodiment.

FIG. 4B is a block diagram illustrating a system 400B, in accordance with an embodiment. Of note, the components shown in system 400A of FIG. 4A may be integrated with the control module 108 of FIGS. 1 and 2. As such, FIG. 4B illustrates the integration of the components of the system 400A of FIG. 4A with the components of control module 108 shown in FIGS. 1 and 2, as well as additional optional components, in accordance with embodiments.

For example, system 400B includes one or more additional components, in various embodiments, in addition to the set of sensors 422, the converting module 216 and the cryptographic key generator 214. As illustrated in FIG. 4B, the one or more additional components include one or more of the following components: a communication subsystem 208; a data storage unit 402; a decrypting module 408; an authentication module 410; a comparer 412; a public cryptographic key generator 404; a private cryptographic key generator 406; an ADC 424; a data processing module 426; and at least one external device 414 such as a programmer 120 and/or a monitor 420. System 400B further includes, in various embodiments, one or more of the following components: a sensor interface 200; a detection subsystem 202; a memory subsystem 204; a CPU 210; a power supply 206; and a clock supply 212.

In one embodiment, the communication subsystem 208 is coupled with the cryptographic key generator 214. The communication subsystem 208 provides a communication interface between the IMD 106 and at least one external device 414. The at least one external device 414 is a programmer 120, in one instance. In another embodiment, the at least one external device 414 is a monitor 420. It should be appreciated, and as has been described herein, the at least one external device 414 may be more than one external device, as well as a combination of various different external devices. In some embodiments, the programmer 120 includes a receiver 416 and a message encryptor 418. The receiver 416 receives a public cryptographic key from the IMD 106. The message encryptor 418 encrypts a message utilizing a first private cryptographic key, wherein the first private cryptographic key is generated utilizing the public cryptographic key and a predetermined cryptographic key generation protocol.

In one embodiment, the decrypting module 408 is coupled with the communication subsystem 208 and decrypts a message received from the at least one external device 414. In another embodiment, the authentication module 410 is coupled with the decrypting module 408 and determines an authentication status of the at least one external device 414, based on the decrypted message.

The comparer 412, in various embodiments, is coupled with the authentication module 410 and compares a stored pass-code with the decrypted message. A positive verification of the authentication status is indicated if the decrypted message matches the stored pass-code. A negative verification of the authentication status is indicated if the decrypted message differs from the stored pass-code.

In yet another embodiment, the data storage unit 402 is coupled with the set of sensors 422, and stores the sensed dynamic biometric activity. Of note, FIG. 4B shows the data storage unit 402 residing in the memory subsystem 204. However, it should be noted that the data storage unit 402 may reside external to the memory subsystem 204.

In one embodiment, the converting module 216 includes an ADC 424. The ADC 424 transforms the sensed dynamic biometric activity into a digital representation. In another embodiment, the converting module 216 includes a data processing module 426 that is coupled with the ADC 424 and receives converted data (digital representations). The cryptographic key generator 214 is coupled with the converting module 216 and generates a cryptographic key utilizing the digital representation, as has already been described herein.

In one embodiment, the cryptographic key generator 214 includes one or more of the following: a public cryptographic key generator 404 that generates a public cryptographic key utilizing the digital representation; and a private cryptographic key generator 406 that generates a private cryptographic key utilizing the public cryptographic key and a predetermined cryptographic key generation protocol. Of note, the predetermined cryptographic key generation protocol referred to herein is that cryptographic key generation protocol that is commonly known to one of ordinary skill in the art and capable of being used with the generated public cryptographic key described herein to accomplish the functions described herein.

Example Methods for Establishing Secure Communication Between an IMD and an External Device With reference to FIGS. 5, 6 and 7, flow diagrams 500, 600 and 700 illustrate example procedures used by various embodiments. Flow diagrams 500, 600 and 700 include processes and operations that, in various embodiments, are carried out by one or more processors (e.g., CPU(s) of FIG. 2) under the control of computer-readable and computer-executable instructions. The computer-readable and computer-executable instructions reside, for example, in tangible data storage features such as memory subsystem 204 and/or a data storage unit 402. The computer-readable and computer-executable instructions, which may reside on computer readable media, are used to control or operate in conjunction with, for example, one or more components of the control module 108 of FIGS. 1, 2 and 5 and/or one or more processors (see CPU of FIGS. 2 and 4B).

Although specific procedures are disclosed in flow diagrams 500, 600 and 700, such procedures are examples. That is, embodiments are well suited to performing various other operations or variations of the operations recited in the processes of flow diagrams 500, 600, and 700. Likewise, in some embodiments, the operations in flow diagrams 500, 600, and 700 may be performed in an order different than presented, not all of the operations described in one or more of these flow diagrams may be performed, and/or one or more additional operations may be added.

Figure 5A:
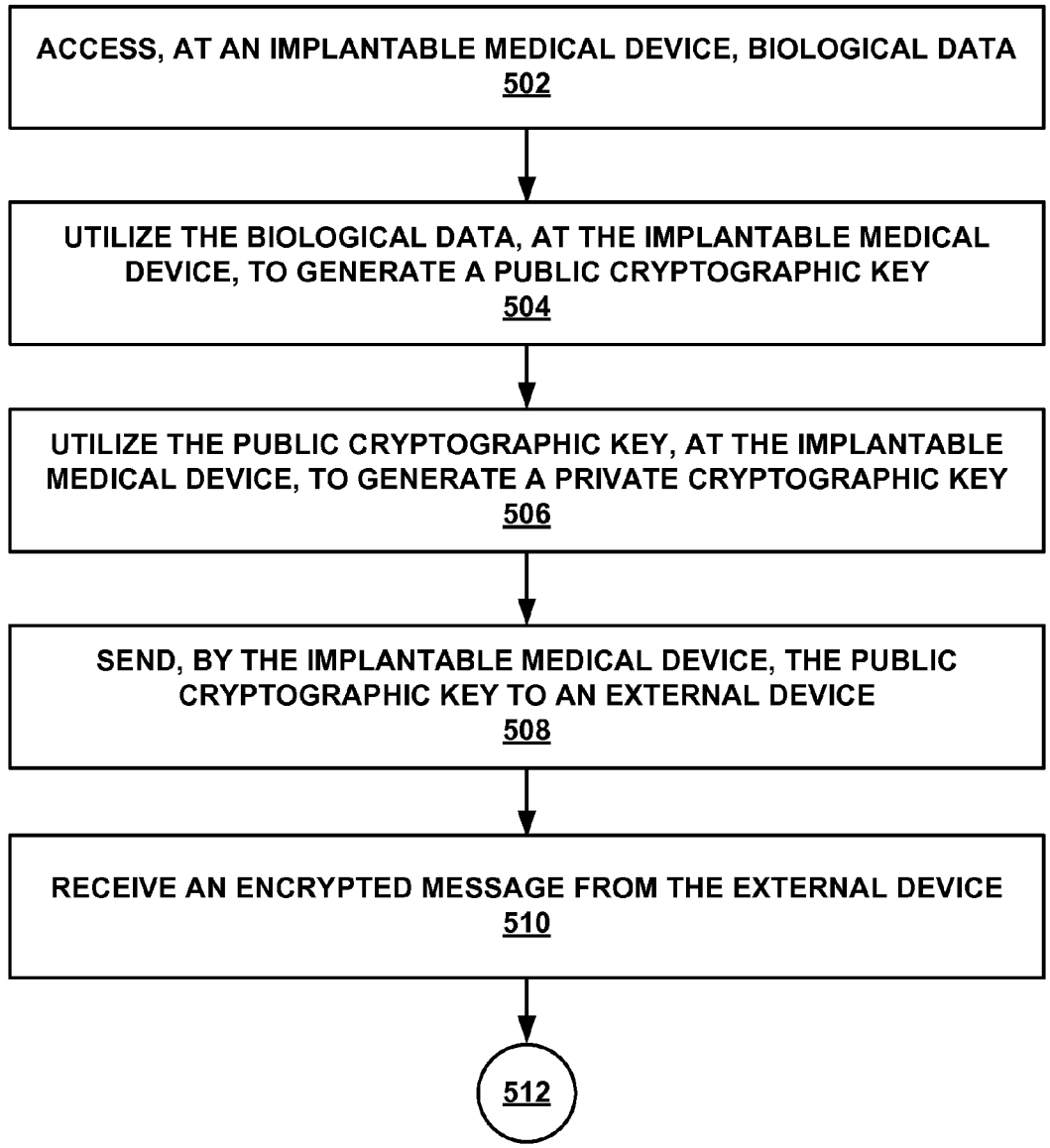
FIGS. 5A and 5B show a flow diagram illustrating an example method for establishing a secure communication between an implantable medical device and an external device, in accordance with an embodiment.
Figure 5B:
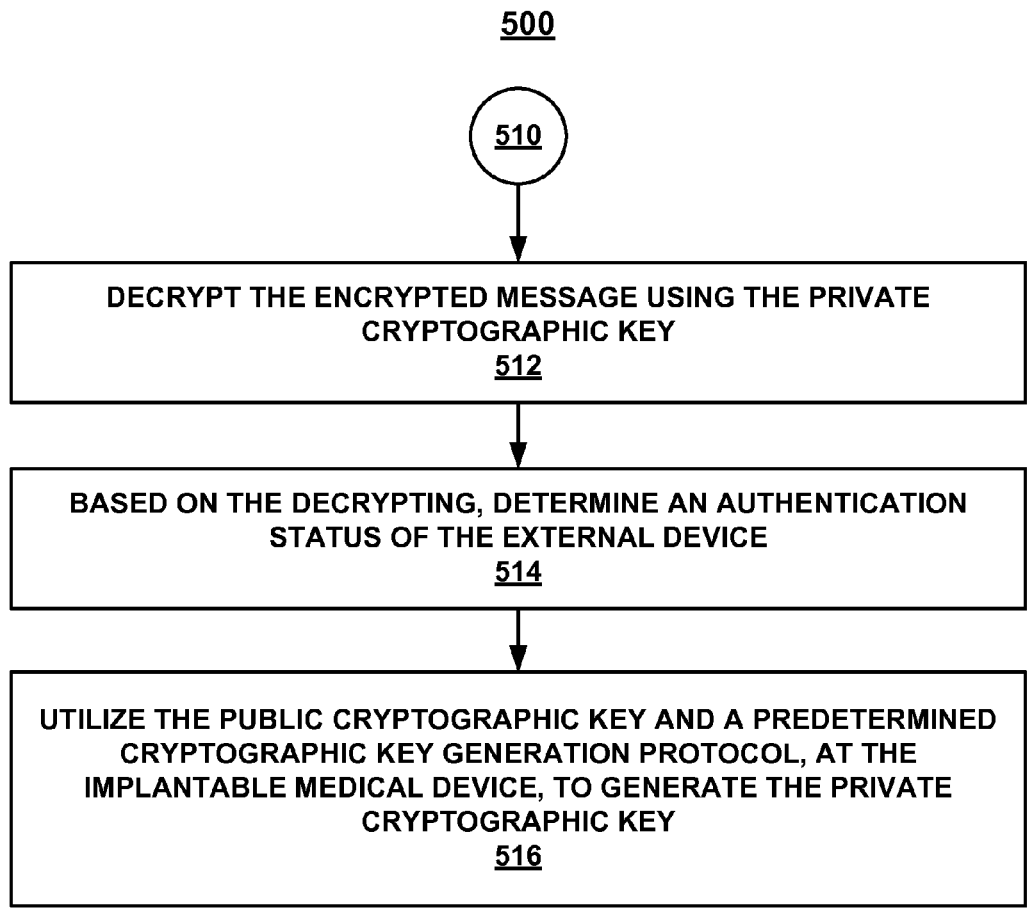

FIGS. 5A and 5B show a flow diagram 500 of an example method for establishing a secure communication between an IMD and an external device, in accordance with an embodiment. Reference will be made to FIGS. 1, 2 and 4B to facilitate the explanation of the operations of the method of flow diagram 500.

Referring to FIGS. 1, 2, 4B and 5A, at operation 502, in one embodiment, biological data is accessed at the IMD 106. Biological data refers to data associated with the body, including, but limited to, the following: biological signals (e.g., EEG and ECoG waveforms); body movement; blood flow; blood concentration; physiological conditions; and static biometric data.

At operation 504, in one embodiment, the biological data is utilized, at the IMD 106, to generate a public cryptographic key. For example, while the random number is generated by virtue of the accessing of biological data by the IMD 106, the last few bytes of the digital representation of the biological data are then used as the public cryptographic key. In another example and as described herein, using data converted from biological data to a digital representation, the line length between subsequent ECoG samples is computed. Some portion of the computed line length may be then utilized as a random number in the creation of a public cryptographic key. In one embodiment, for example, the last four bytes of the line length may then be used to create a four byte public cryptographic key number. In another embodiment, the first four bytes of the line length may be used to create a four byte public cryptographic key. In another embodiment, the first byte and the last three bytes of the line length may be used to create a four byte public cryptographic key. A greater or lesser number of bits of the line length may be used, in various embodiments. In other embodiments, data snippets from other accessed biological data may be similarly utilized as a random number in the generation of a public cryptographic key.

At operation 506, in one embodiment and as described herein, the public cryptographic key is utilized at the IMD 106 to generate a private cryptographic key. At operation 508, in one embodiment and as described herein, the public cryptographic key is sent to an external device by the IMD 106. At operation 510 in one embodiment and as described herein, an encrypted message is received from the external device.

Referring now to FIGS. 1, 2, 4B and 5B, at operation 512, in one embodiment and as described herein, the encrypted message is decrypted using the private cryptographic key. At operation 514, in one embodiment and as described herein, based on the decrypting, an authentication status of the external device is determined. At operation 516, in one embodiment and as described herein, a private cryptographic key is generated at the IMD 106, utilizing the public cryptographic key and a predetermined cryptographic key generation protocol.

Figure 6A:
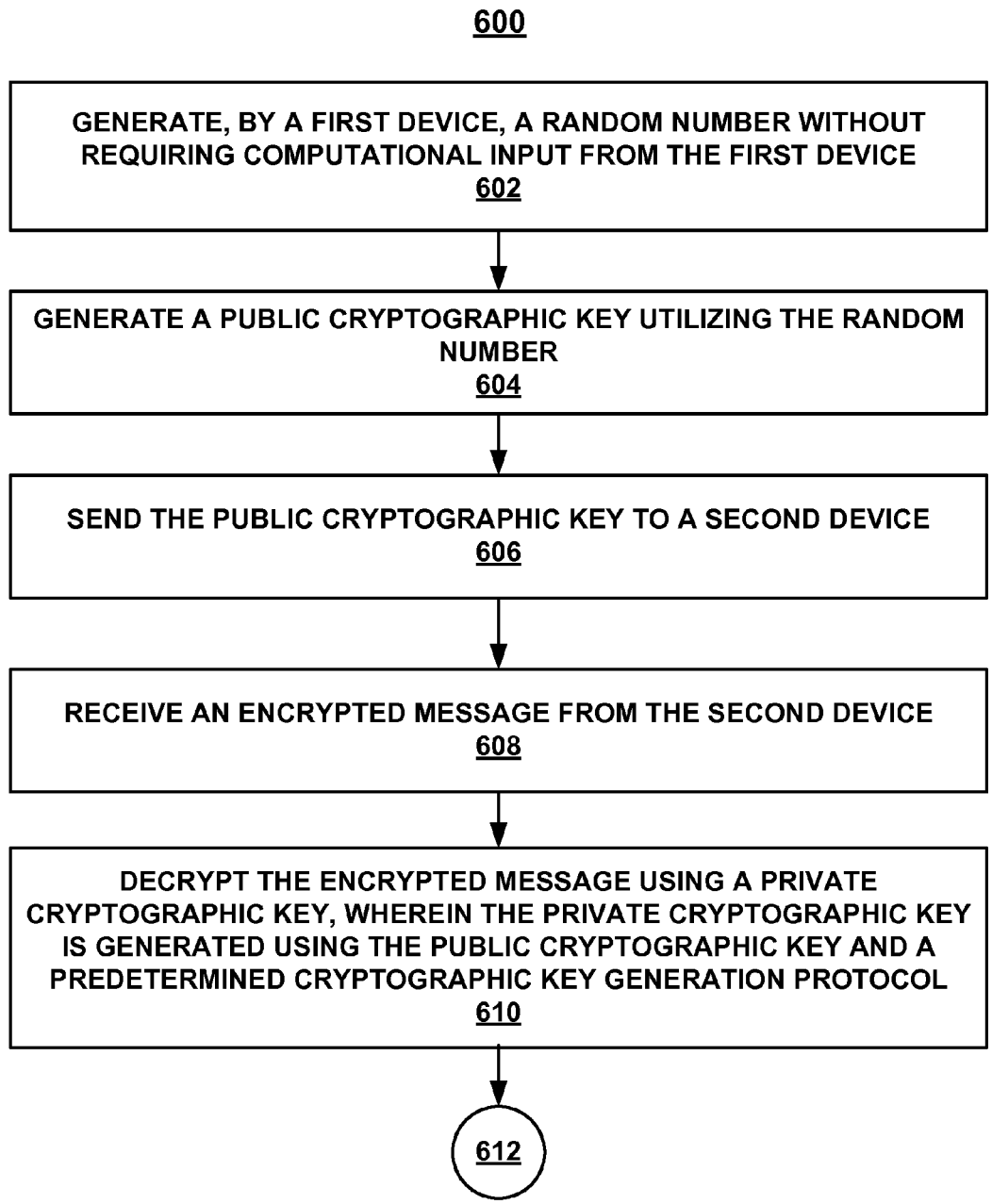
FIGS. 6A and 6B show a flow diagram illustrating an example method for establishing a secure communication between an implantable medical device an external device, in accordance with an embodiment.
Figure 6B:
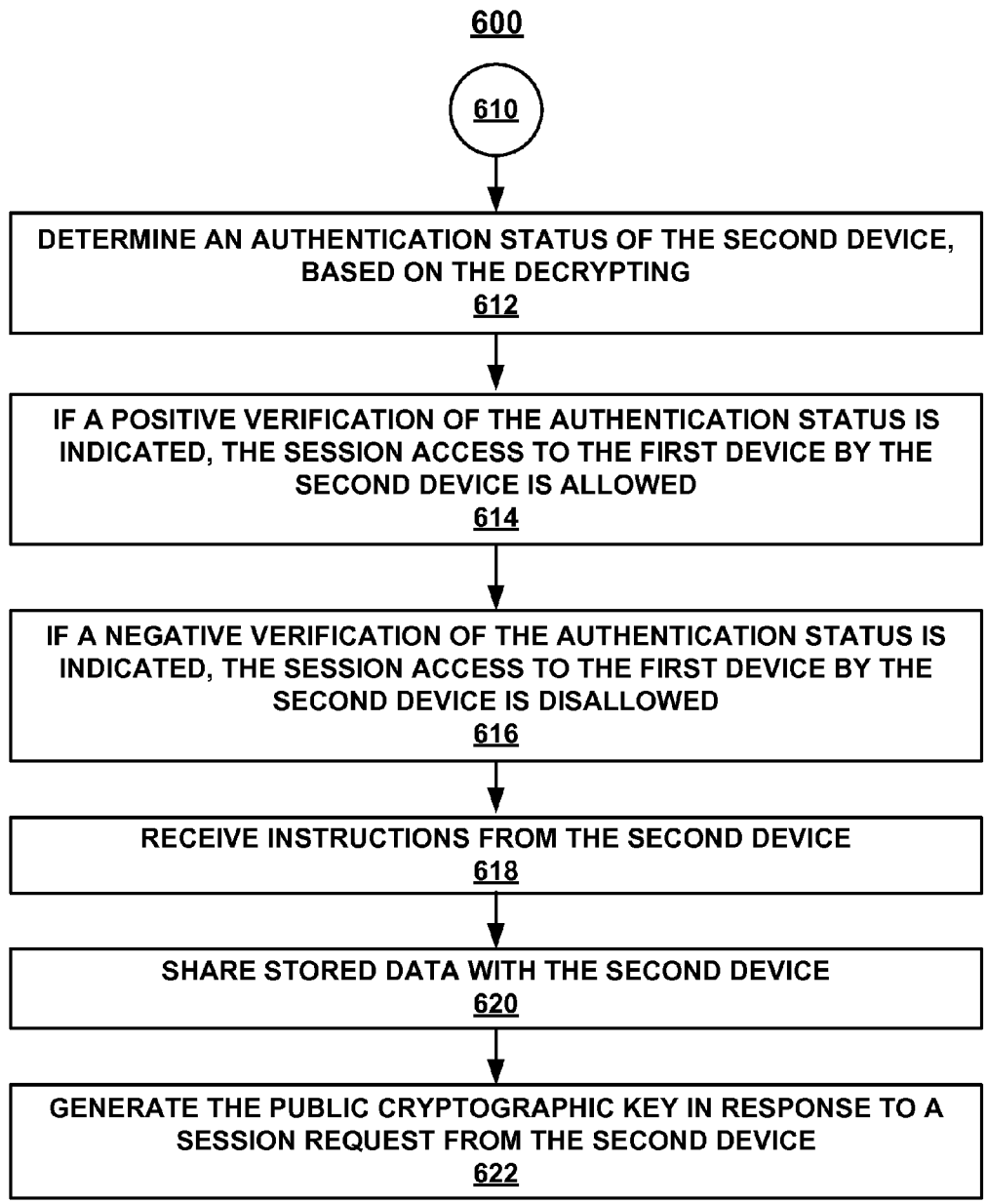

FIGS. 6A and 6B show a flow diagram 600 of an example method for establishing a secure communication between an IMD and an external device, in accordance with an embodiment. Reference will be made to FIGS. 1, 2 and 4B to facilitate the explanation of the operations of the method of flow diagram 500.

Referring now to FIGS. 1, 2, 4B and 6A, at operation 602 and as described herein, a random number is generated by a first device, without requiring computational input from the first device. In contrast, current methods for calculating a random number for using as a public cryptographic key require computational input from the device generating the random number. The term, "computational input", in the context of the first device, refers to performing calculations to generate the random number. In one embodiment, biological signals that are stored at the IMD 106 (in digital form) are utilized to generate the public cryptographic key. The "first device" may be the IMD 106, in one embodiment.

At operation 604, in one embodiment and as described herein, a public cryptographic key is generated utilizing the random number. At operation 606, in one embodiment and as described herein, the public cryptographic key is sent to a second device, such as, but not limited to, one or more programmers and/or one or more monitors. At operation 608, in one embodiment and as described herein, an encrypted message is received from the second device. Then, at operation 610, in one embodiment and as described herein, the encrypted message is decrypted using a private cryptographic key, wherein the private cryptographic key is generated using the public cryptographic key and a predetermined cryptographic key generation protocol. At operation 612, in one embodiment and as described herein, based on the decrypting, an authentication status of the second device is determined.

Referring now to FIGS. 1, 2, 4B and 6B, at operation 614, in one embodiment, if a positive verification of the authentication status is indicated, the session access to the first device by the second device is allowed. Thus, if the pass-code decrypted by the first device matches the golden pass-code held in storage by the first device, then a positive verification of the authentication status is indicated and the second device is given session access. The term, "session access", refers to allowing access to a session with the first device, such as sharing information between the first and second device and/or programming of the first device by the second device. The term, "indicated", in the context of indicating a positive verification (and a negative verification, as will be explained below), refers to the actions, such as, but not limited to the following: automatically allowing access to the IMD 106 by the at least one external device 414; automatically disallowing access by the at least one external device 414 to the IMD 106; and providing a type of signal (e.g., audio, visual), internal and/or external to the machine.

At operation 616, however, in one embodiment, if a negative verification of the authentication status is indicated, the session access to the first device by the second device is disallowed. Thus, if the pass-code decrypted by the first device does not match the golden pass-code held in storage by the first device, then a negative verification of the authentication status is indicated, and the interaction between the first device and the second device is terminated, and any request for a new interrogation by the second device will require acquiring a new public cryptographic key from the first device. In some embodiments, if session access is disallowed, repeated attempts at communication may be locked out for some predetermined amount of time.

At operation 618, in one embodiment, instructions are received from the second device. These instructions may be, but are not limited to, programming instructions such as parameter changes to the IMD. At operation 620, in one embodiment, stored data is shared with the second device. For example, data, such as biological signals stored on the IMD, may be communicated between the first and second device.

At operation 622, in one embodiment, in response to a session request from the second device, the first device generates the public cryptographic key.

Figure 7A:
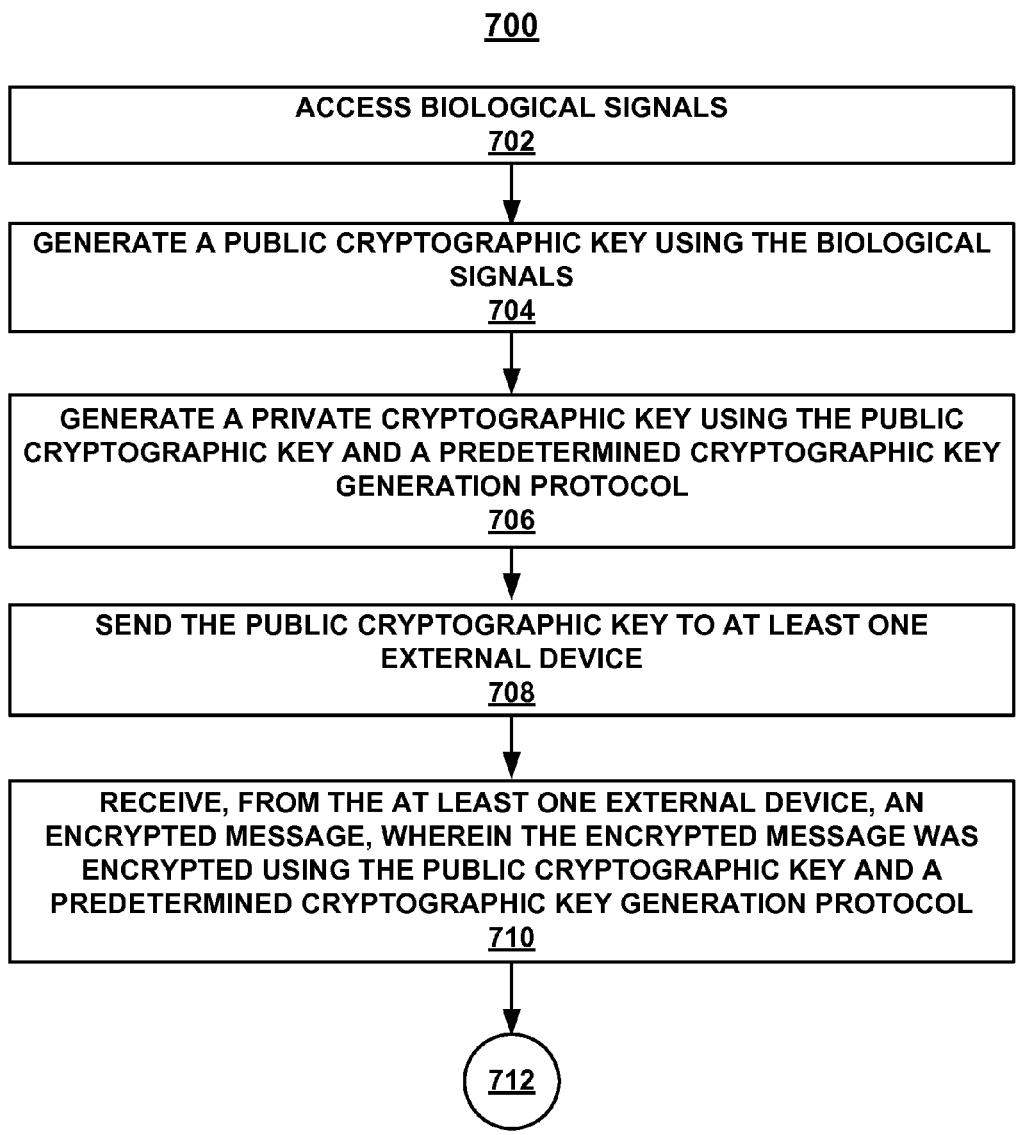
FIGS. 7A and 7B show a flow diagram illustrating an example method for establishing a secure communication between an implantable medical device and an external device, in accordance with an embodiment.
Figure 7B:
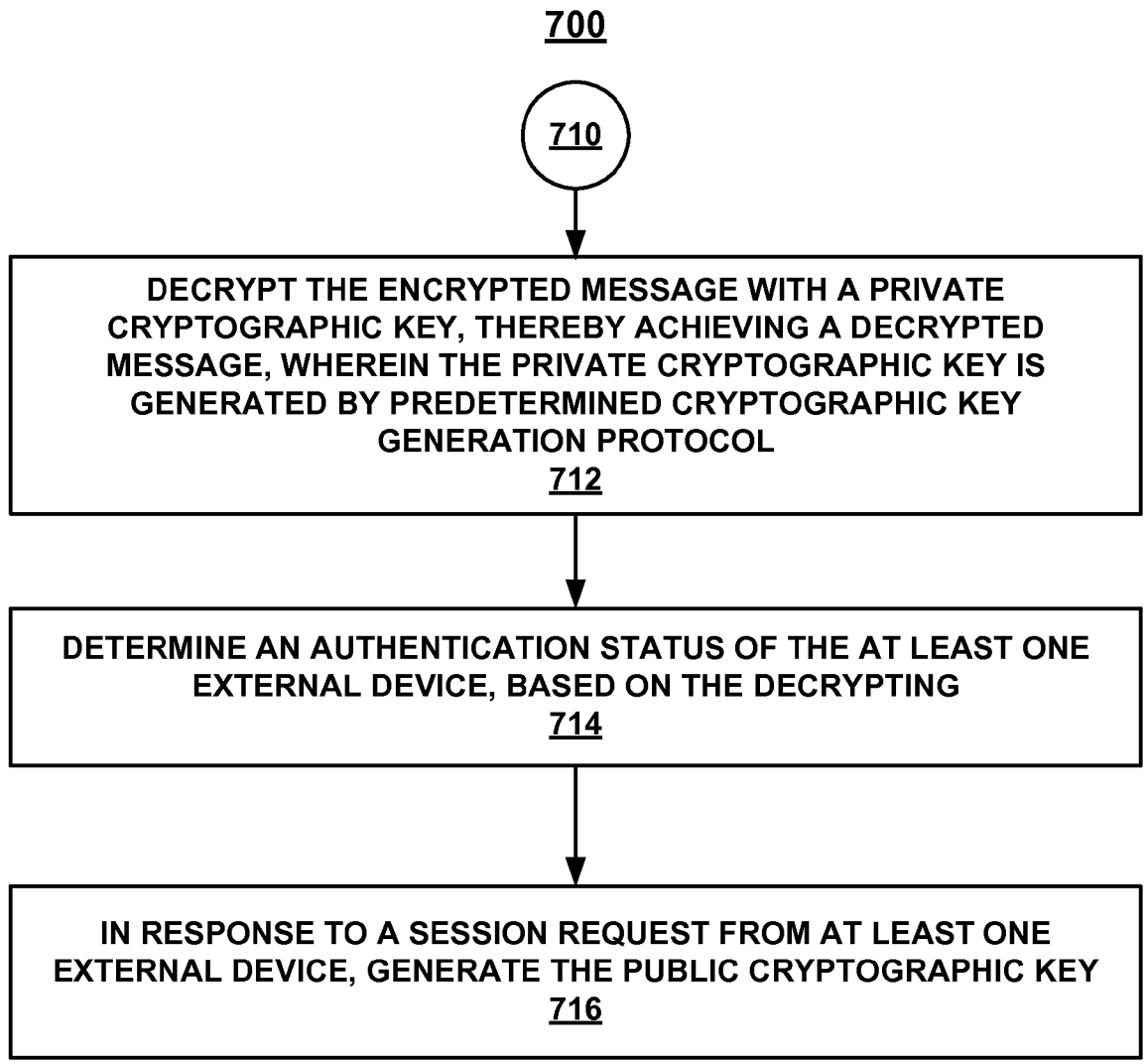

FIGS. 7A and 7B show a flow diagram 700 of an example method for establishing a secure communication between an IMD and an external device, in accordance with an embodiment. Reference will be made to FIGS. 1, 2 and 4B to facilitate the explanation of the operations of the method of flow diagram 700.

Referring to FIGS. 1, 2, 4B and 7A, at operation 702, in one embodiment and as described herein, biological signals are accessed. At operation 704 and as described herein, in one embodiment and as is described herein, a public cryptographic key is generated using the biological signals.

At operation 706, in one embodiment and as described herein, a private cryptographic key is generated using the public cryptographic key and a predetermined cryptographic key generation protocol. At operation 708, in one embodiment and as described herein, the public cryptographic key is sent to at least one external device. At operation 710, in one embodiment and as described herein, an encrypted message is received from the at least one external device, wherein the encrypted message was encrypted using the public cryptographic key and a predetermined cryptographic key generation protocol.

Referring to FIGS. 1, 2, 4B and 7B, at operation 712, in one embodiment and as described herein, the encrypted message is decrypted with the private cryptographic key, thereby achieving a decrypted message, wherein the private cryptographic key is generated by the implantable medical device using the public cryptographic key and a predetermined cryptographic key generation protocol.

At operation 714, in one embodiment and as described herein, an authentication status of the at least one external device is determined, based on the decrypting of operation 712. At operation 716, in one embodiment and as described herein, in response to a session request from the at least one external device, generating the public cryptographic key.

Various example embodiments are thus described. All statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope, therefore, is not intended to be limited to the embodiments shown and described herein. Rather, the scope and spirit is embodied by the appended claims.

What is claimed is:

1. A non-transitory computer readable storage medium having stored thereon, computer-executable instructions that, when executed by a computer, cause the computer to perform a method for establishing secure communication between an implantable medical device and an external device, the method comprising:

accessing, at an implantable medical device, biological data;

utilizing the biological data, at the implantable medical device, to generate a public cryptographic key, wherein the public cryptographic key corresponds to a portion of a random number culled directly from a representation of the biological data; and utilizing the public cryptographic key, at the implantable medical device, to generate a private cryptographic key.

2. The non-transitory computer readable storage medium of claim 1, wherein the method further comprises:

sending, by the implantable medical device, the public cryptographic key to an external device.

3. The non-transitory computer readable storage medium of claim 2, wherein the method further comprises:

receiving an encrypted message from the external device.

4. The non-transitory computer readable storage medium of claim 3, wherein the method further comprises:

decrypting the encrypted message using the private cryptographic key.

5. The non-transitory computer readable storage medium of claim 4, wherein the method further comprises:

based on the decrypting, determining an authentication status of the external device.

6. The non-transitory computer readable storage medium of claim 1, wherein the method further comprises:

utilizing the public cryptographic key and a predetermined cryptographic key generation protocol, at the implantable medical device, to generate the private cryptographic key.

7. A non-transitory computer readable storage medium having stored thereon, computer-executable instructions that, when executed by a computer, cause the computer to perform a method for establishing secure communication between an implantable medical device and an external device, the method comprising:

generating a random number by a first device without requiring computational input from the first device, the random number culled directly from a representation of biological signals sensed by the implantable medical device;

generating a public cryptographic key utilizing the random number;

sending the public cryptographic key to a second device;

receiving an encrypted message from the second device;

decrypting the encrypted message using a private cryptographic key, the private cryptographic key being generated using the public cryptographic key and a predetermined cryptographic key generation protocol; and based on the decrypting, determining an authentication status of the second device.

8. The non-transitory computer readable storage medium of claim 7, wherein the method further comprises:

if a positive verification of the authentication status is indicated, allowing session access to the first device by the second device.

9. The non-transitory computer readable storage medium of claim 7, wherein the method further comprises:

receiving instructions from the second device.

10. The non-transitory computer readable storage medium of claim 7, wherein the method further comprises:

sharing stored data with the second device.

11. The non-transitory computer readable storage medium of claim 7, wherein the method further comprises:

if a negative verification of the authentication status is indicated, disallowing session access to the first device by the second device.

12. The non-transitory computer readable storage medium of claim 7, wherein the method further comprises:

in response to a session request from the second device, the generating the public cryptographic key by the first device.

13. The non-transitory computer readable storage medium of claim 7, wherein the generating a random number by a first device without requiring computational input from the first device comprises:

generating the random number by the first device that is an implantable medical device without requiring the computational input from the first device.

14. A method for establishing secure communication between an implantable medical device and an external device, the method comprising:

accessing, at the implantable medical device, biological signals; and generating, at the implantable medical device, a public cryptographic key wherein the public cryptographic key corresponds to a portion of a random number culled directly from a representation of the biological signals.

15. The method of claim 14, further comprising:

generating a private cryptographic key using the public cryptographic key and a predetermined cryptographic key generation protocol.

16. The method of claim 14, further comprising:

sending the public cryptographic key to at least one external device.

17. The method of claim 16, further comprising:

receiving, from the at least one external device, an encrypted message, wherein the encrypted message was encrypted using the public cryptographic key and a predetermined cryptographic key generation protocol.

18. The method of claim 17, further comprising:

decrypting the encrypted message with a private cryptographic key, thereby achieving a decrypted message, wherein the private cryptographic key is generated by the implantable medical device using the public cryptographic key and a predetermined cryptographic key generation protocol.

19. The method of claim 18, further comprising:

determining an authentication status of the at least one external device, based on the decrypting.

20. The method of claim 19, wherein the determining an authentication status of the device comprises:

comparing the decrypted message with a stored pass-code;

indicating a positive verification of the authentication status if the decrypted message matches the stored pass-code; and indicating a negative verification of the authentication status if the decrypted message differs from the stored pass-code.

21. The method of claim 14, further comprising:

in response to a session request from at least one external device, the generating the public cryptographic key.

22. A system for establishing secure communication between devices, the system comprising:

a set of sensors configured for sensing dynamic biometric activity;

a converting module coupled with the set of sensors, the converting module configured for converting a portion of sensed dynamic biometric activity to a digital representation; and a cryptographic key generator coupled with the converting module, the cryptographic key generator configured for generating a cryptographic key utilizing the digital representation, wherein the cryptographic key corresponds to a portion of a random number culled directly from the digital representation.

23. The system of claim 22, further comprising:
a communication subsystem coupled with the cryptographic key generator, the communication subsystem configured for providing a communication interface between an implantable medical device and at least one external device.

24. The system of claim 23, wherein the at least one external device is a programmer.

25. The system of claim 24, wherein the programmer comprises:
a receiver configured for receiving a public cryptographic key from an implantable medical device that comprises the cryptographic key generator; and
a message encryptor configured for encrypting a message utilizing a first private cryptographic key, wherein the first private cryptographic key is generated utilizing the public cryptographic key and a predetermined cryptographic key generation protocol, wherein the public cryptographic key is sent to the programmer via the communication subsystem.

26. The system of claim 23, wherein the at least one external device is a monitor.

27. The system of claim 23, further comprising:
a decrypting module configured for decrypting a message received from the at least one external device, thereby achieving a decrypted message.

28. The system of claim 27, further comprising:
an authentication module coupled with the decrypting module, the authentication module configured for determining an authentication status of the at least one external device, based on the decrypted message.

29. The system of claim 28, wherein the authentication module comprises:
a comparer coupled with the authentication module, the comparer configured for comparing a stored pass-code with the decrypted message, indicating a positive verification of the authentication status if the decrypted message matches the stored pass-code, and indicating a negative verification of the authentication status if the decrypted message differs from the stored passcode.

30. The system of claim 22, further comprising:
a data storage unit coupled with the set of sensors, the data storage unit configured for storing the sensed dynamic biometric activity.

31. The system of claim 22, wherein the cryptographic key is a public cryptographic key, and wherein the cryptographic key generator comprises:
a public cryptographic key generator configured for generating the public cryptographic key utilizing the digital representation.

32. The system of claim 31, wherein the cryptographic key is a private cryptographic key, and wherein the cryptographic key generator further comprises:
a private cryptographic key generator configured for generating the private cryptographic key utilizing the public cryptographic key and a predetermined cryptographic key generation protocol.

* * * * *